United States Patent [19]

Nason, II et al.

[11] Patent Number: 5,804,554

[45] Date of Patent: Sep. 8, 1998

[54] CALCIUM CHANNEL BLOCKING POLYPEPTIDES FROM FILISTATA HIBERNALIS

[75] Inventors: Deane M. Nason, II, Norwich; Steven D. Heck, Groton; Robert T. Ronau, Gales Ferry; Nicholas A. Saccomano, Ledyard; Robert A. Volkmann, Mystic, all of Conn.

[73] Assignee: Pfizer Inc., New York, N.Y.

[21] Appl. No.: 379,538

[22] PCT Filed: Apr. 30, 1993

[86] PCT No.: PCT/US93/03921

§ 371 Date: May 3, 1995

§ 102(e) Date: May 3, 1995

[87] PCT Pub. No.: WO93/23428

PCT Pub. Date: Nov. 25, 1993

[51] Int. Cl.[6] .............................. A61K 38/00; C07K 5/00; C07K 7/00

[52] U.S. Cl. ................................................. 514/12; 530/324

[58] Field of Search ............................... 514/12; 530/324, 530/855, 858

[56] References Cited

PUBLICATIONS

Adams et al., *J of Biol. Chem.*, vol. 265, No. 2, pp. 861–867, Jan. 15, 1990.

*Primary Examiner*—Avis M. Davenport
*Attorney, Agent, or Firm*—Peter C. Richardson; Paul H. Ginsburg; Bryan C. Zielinski

[57] ABSTRACT

Polypeptides isolated from the venom of the *Filistata hibernalis* spider block calcium channels in cells of various organisms and are useful in blocking said calcium channels in cells, per se, in the treatment of calcium channel-mediated diseases and conditions and in the control of invertebrate pests.

2 Claims, No Drawings

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: No ( i v ) ANTI-SENSE: No ( v i ) ORIGINAL SOURCE:
        ( A ) ORGANISM: Filistata hibernalis
        ( F ) TISSUE TYPE: venom ( x i ) SEQUENCE DESCRIPTION: SEQ ID NO: 1:

```
Ala  Glu  Cys  Val  Asn  Ile  Tyr  Gln  Pro  Cys  Ser  Thr  Ile  Gly  Leu  Arg
 1              5                        10                       15
Cys  Cys  Tyr  Gly  Ala  Arg  Cys  Tyr  Cys  Lys  Glu  Lys  Leu  Asn  Cys  Arg
               20                       25                            30
Tyr  Asn  Arg  Ser  Thr  Arg  Lys  Arg  Asp  Cys  Gly  Trp  Ser  Ser  Tyr  Asp
          35                       40                       45
Cys  Lys  Cys  Asp  Tyr  Thr  Trp  Met  His  Arg  Ile  Asp  Asp  Trp  Arg  Glu
     50                       55                       60
Gly  Tyr  Ser  Cys  Tyr  Cys  Lys  Glu
 65                      70
```

( 2 ) INFORMATION FOR SEQ ID NO: 2:

( i ) SEQUENCE CHARACTERISTICS:
        ( A ) LENGTH: 74 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: No ( i v ) ANTI-SENSE: No ( v i ) ORIGINAL SOURCE:
        ( A ) ORGANISM: Filistata hibernalis
        ( F ) TISSUE TYPE: venom ( x i ) SEQUENCE DESCRIPTION: SEQ ID NO: 2:

```
Ala  Glu  Cys  Leu  Met  Val  Gly  Asp  Thr  Ser  Cys  Val  Pro  Arg  Leu  Gly
 1              5                        10                       15
Arg  Arg  Cys  Cys  Tyr  Gly  Ala  Trp  Cys  Tyr  Cys  Asp  Gln  Gln  Leu  Ser
               20                       25                            30
Cys  Arg  Arg  Val  Gly  Arg  Lys  Gln  Gln  Cys  Gly  Trp  Arg  Glu  Val  Asn
          35                       40                       45
Cys  Lys  Cys  Asp  Trp  Ser  Trp  Ser  Gln  Arg  Ile  Asp  Asp  Trp  Arg  Ala
     50                       55                       60
Asp  Tyr  Ser  Cys  Lys  Cys  Pro  Glu  Asp  Gln
 65                      70
```

( 2 ) INFORMATION FOR SEQ ID NO: 3:

( i ) SEQUENCE CHARACTERISTICS:
        ( A ) LENGTH: 74 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: No ( i v ) ANTI-SENSE: No ( v i ) ORIGINAL SOURCE:
        ( A ) ORGANISM: Filistata hibernalis
        ( F ) TISSUE TYPE: venom ( x i ) SEQUENCE DESCRIPTION: SEQ ID NO: 3:

```
Ala Glu Cys Leu Met Val Gly Asp Thr Ser Cys Val Pro Arg Leu Gly
 1               5                  10                  15
Arg Arg Cys Cys Tyr Gly Ala Trp Cys Tyr Cys Asp Gln Gln Leu Ser
            20                  25                  30
Cys Arg Arg Val Gly Arg Lys Arg Glu Cys Gly Trp Val Glu Val Asn
        35                  40                  45
Cys Lys Cys Gly Trp Ser Trp Ser Gln Arg Ile Asp Asp Trp Arg Ala
    50                  55                  60
Asp Tyr Ser Cys Lys Cys Pro Glu Asp Gln
65                  70
```

( 2 ) INFORMATION FOR SEQ ID NO: 4:

( i ) SEQUENCE CHARACTERISTICS:
        ( A ) LENGTH: 74 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: No ( i v ) ANTI-SENSE: No ( v i ) ORIGINAL SOURCE:
        ( A ) ORGANISM: Filistata hibernalis
        ( F ) TISSUE TYPE: venom ( x i ) SEQUENCE DESCRIPTION: SEQ ID NO: 4:

```
Ala Glu Cys Leu Met Val Gly Asp Thr Ser Cys Val Pro Arg Leu Gly
 1               5                  10                  15
Arg Arg Cys Cys Tyr Gly Ala Trp Cys Tyr Cys Asp Gln Gln Leu Ser
            20                  25                  30
Cys Arg Arg Val Gly Arg Lys Arg Glu Cys Gly Trp Val Glu Val Asn
        35                  40                  45
Cys Lys Cys Gly Trp Ser Trp Ser Gln Arg Ile Asp Asp Trp Arg Ala
    50                  55                  60
Asp Tyr Asn Cys Lys Cys Pro Glu Asp Gln
65                  70
```

( 2 ) INFORMATION FOR SEQ ID NO: 5:

( i ) SEQUENCE CHARACTERISTICS:
        ( A ) LENGTH: 74 amino acids
        ( B ) TYPE: amino acid
        ( C ) STRANDEDNESS: single
        ( D ) TOPOLOGY: linear (i i) MOLECULE TYPE: protein (i i i) HYPOTHETICAL: No (i v) ANTI-SENSE: No (v i) ORIGINAL SOURCE:
    (A) ORGANISM: Filistata hibernalis
    (F) TISSUE TYPE: venom (x i) SEQUENCE DESCRIPTION: SEQ ID NO: 5:

```
Ala Glu Cys Leu Met Ile Gly Asp Thr Ser Cys Val Pro Arg Leu Gly
 1               5                  10                 15
Arg Arg Cys Cys Tyr Gly Ala Trp Cys Tyr Cys Asp Gln Gln Leu Ser
            20                  25                 30
Cys Arg Arg Val Gly Arg Lys Arg Glu Cys Gly Trp Val Glu Val Asn
        35                  40                 45
Cys Lys Cys Gly Trp Ser Trp Ser Gln Arg Ile Asp Asp Trp Arg Ala
    50                  55                 60
Asp Tyr Ser Cys Lys Cys Pro Glu Asp Gln
65                  70
```

(2) INFORMATION FOR SEQ ID NO: 6:

(i) SEQUENCE CHARACTERISTICS:
        (A) LENGTH: 72 amino acids
        (B) TYPE: amino acid
        (C) STRANDEDNESS: single
        (D) TOPOLOGY: linear (i i) MOLECULE TYPE: protein (i i i) HYPOTHETICAL: No (i v) ANTI-SENSE: No (v i) ORIGINAL SOURCE:
    (A) ORGANISM: Filistata hibernalis
    (F) TISSUE TYPE: venom (x i) SEQUENCE DESCRIPTION: SEQ ID NO: 6:

```
Ala Glu Cys Val Asn Ile Tyr Gln Pro Cys Ser Asn Ile Gly Leu Arg
 1               5                  10                 15
Cys Cys Tyr Gly Ala Arg Cys Tyr Cys Lys Glu Lys Leu Ser Cys Arg
            20                  25                 30
Tyr Asn Arg Val Thr Arg Lys Arg Asp Cys Gly Trp Ser Ser Tyr Asp
        35                  40                 45
Cys Lys Cys Asp Tyr Thr Trp Met His Arg Ile Asp Asp Trp Leu Asp
    50                  55                 60
Gly Tyr Ser Cys Tyr Cys Lys Glu
65                  70
```

(2) INFORMATION FOR SEQ ID NO: 7:

(i) SEQUENCE CHARACTERISTICS:
        (A) LENGTH: 73 amino acids
        (B) TYPE: amino acid
        (C) STRANDEDNESS: single
        (D) TOPOLOGY: linear (i i) MOLECULE TYPE: protein (i i i) HYPOTHETICAL: No (i v) ANTI-SENSE: No (v i) ORIGINAL SOURCE:
    (A) ORGANISM: Filistata hibernalis (F) TISSUE TYPE: venom (xi) SEQUENCE DESCRIPTION: SEQ ID NO: 7:

| Glu | Glu | Lys | Lys | Cys | Lys | Leu | Ile | Asp | Glu | Pro | Cys | Ser | Asn | Lys | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Ile | Ile | Cys | Cys | Lys | Gly | Ala | Arg | Cys | Val | Cys | Asn | Asp | Val | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Gly | Thr | Ser | Lys | Asp | Tyr | Leu | Gly | Arg | Asn | Ile | Pro | Ala | Phe | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Val | Cys | Lys | Cys | Asp | Trp | Ser | Tyr | Pro | Ala | Tyr | Leu | Lys | Asp | Leu |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ala | Thr | Phe | Phe | Asn | Cys | Asn | Cys | Arg |
|-----|-----|-----|-----|-----|-----|-----|-----|-----|
| 65  |     |     |     |     | 70  |     |     |     |

CALCIUM CHANNEL BLOCKING POLYPEPTIDES FROM FILISTATA HIBERNALIS

This is a national stage application, filed pursuant to 35 U.S.C. §371, of PCT international application Ser. No. PCT/US93/03921, filed Apr. 30, 1993, published as WO93/23428 Nov. 25, 1993.

BACKGROUND OF THE INVENTION

This invention relates to polypeptides found in the venom of the *Filistata hibernalis* spider and to polypeptides. having substantially the same amino acid sequence and substantially the same activity as said polypeptides. The polypeptides and the pharmaceutically acceptable salts thereof block calcium channels in cells including neuronal and muscle cells of various organisms including invertebrates and vertebrates. This invention also relates to the use of said polypeptides and their salts in blocking calcium channels in cells such as cells in the nervous and muscular system of an organism, per se, and in the treatment of calcium channel mediated diseases and conditions in a mammal. Further, this invention relates to compositions comprising said polypeptides and salts thereof.

Compounds which are calcium antagonists have a variety of utilities. Calcium antagonists can find clinical application in the treatment of such conditions as angina, hypertension, cardiomyopathies, supraventricular arrhythmias, aesophogeal achalasia, premature labor and Raynaud's disease among others. See W. G. Nayler, *Calcium Antagonists*, Academic Press, Harcourt Brace Jovanovich Publishers, New York, N.Y. 1988, the teachings of which are incorporated herein by reference. Further, such compounds are useful in the study of the physiology of cells such as neuronal and muscle cells.

SUMMARY OF THE INVENTION

This invention concerns polypeptides found to be present in the venom of the *Filistata hibernalis* spider. The polypeptides of this invention and the fractions in which they are present according to this invention are as follows.

I. Filistata peptide 10 has the following N-terminal amino acid sequence, SEQ ID NO:1.
$H_2N$-Ala-Glu-Cys-Val-Asn-lle-Tyr-Gln-Pro-Cys-Ser-Thr-lle-Gly-Leu-Arg-Cys-Cys-Tyr-Gly- Ala-Arg-Cys-Tyr-Cys-Lys-Glu-Lys-Leu-Asn-Cys-Arg-Tyr-Asn-Arg-Ser-Thr-Arg-Lys-Arg- Asp-Cys-Gly-Trp-Ser-Ser-Tyr-Asp-Cys-Lys-Cys-Asp-Tyr-Thr-Trp-Met-His-Arg-lle-Asp- Asp-Trp-Arg-Glu-Gly-Tyr-Ser-Cys-Tyr-Cys-Lys-Glu-$CO_2H$ II. Filistata peptide 12 has the following N-terminal amino acid sequence, SEQ ID NO:2.
$H_2N$-Ala-Glu-Cys-Leu-Met-Val-Gly-Asp-Thr-Ser-Cys-Val-Pro-Arg-Leu-Gly-Arg-Arg-Cys- Cys-Tyr-Gly-Ala-Trp-Cys-Tyr-Cys-Asp-Gln-Gln-Leu-Ser-Cys-Arg-Arg-Val-Gly-Arg-Lys- Gln-Gln-Cys-Gly-Trp-Arg-Glu-Val-Asn-Cys-Lys-Cys-Asp-Trp-Ser-Trp-Ser-Gln-Arg-lle- Asp-Asp-Trp-Arg-Ala-Asp-Tyr-Ser-Cys-Lys-Cys-Pro-Glu-Asp-Gln-$CO_2H$ III. Filistata peptide 13-1 has the following N-terminal amino acid sequence, SEQ ID NO:3.
$H_2N$-Ala-Glu-Cys-Leu-Met-Val-Gly-Asp-Thr-Ser-Cys-Val-Pro-Arg-Leu-Gly-Arg-Arg-Cys Cys-Tyr-Gly-Ala-Trp-Cys-Tyr-Cys-Asp-Gln-Gln-Leu-Ser-Cys-Arg-Arg-Val-Gly-Arg-Lys- Arg-Glu-Cys-Gly-Trp-Val-Glu-Val-Asn-Cys-Lys-Cys-Gly-Trp-Ser-Trp-Ser-Gln-Arg-lle- Asp-Asp-Trp-Arg-Ala-Asp-Tyr-Ser-Cys-Lys-Cys-Pro-Glu-Asp-Gin-$CO_2H$ IV. Filistata peptide 13-2 has the following N-terminal amino acid sequence, SEQ ID NO:4.
$H_2N$-Ala-Glu-Cys-Leu-Met-Val-Gly-Asp-Thr-Ser-Cys-Val-Pro-Arg-Leu-Gly-Arg-Arg-Cys- Cys-Tyr-Gly-Ala-Trp-Cys-Tyr-Cys-Asp-Gln-Gln-Leu-Ser-Cys-Arg-Arg-Val-Gly-Arg-Lys- Arg-Glu-Cys-Gly-Trp-Val-Glu-Val-Asn-Cys-Lys-Cys-Gly-Trp-Ser-Trp-Ser-Gln-Arg-lle- Asp-Asp-Trp-Arg-Ala-Asp-Tyr-Asn-Cys-Lys-Cys-Pro-Glu-Asp-Gln-$CO_2H$ V. Filistata peptide 13-3 has the following N-terminal amino acid sequence, SEQ ID NO:5.
$H_2N$-Ala-Glu-Cys-Leu-Met-lie-Gly-Asp-Thr-Ser-Cys-Val-Pro-Arg-Leu-Gly-Arg-Arg-Cys- Cys-Tyr-Gly-Ala-Trp-Cys-Tyr-Cys-Asp-Gln-Gln-Leu-Ser-Cys-Arg-Arg-Val-Gly-Arg-Lys- Arg-Glu-Cys-Gly-Trp-Val-Glu-Val-Asn-Cys-Lys-Cys-Gly-Trp-Ser-Trp-Ser-Gln-Arg-lle- Asp-Asp-Trp-Arg-Ala-Asp-Tyr-Ser-Cys-Lys-Cys-Pro-Glu-Asp-Gln-$CO_2H$ VI. Filistata peptide 13-4 has the following N-terminal amino acid sequence, SEQ ID NO:6.
$H_2N$-Ala-Glu-Cys-Val-Asn-lle-Tyr-Gln-Pro-Cys-Ser-Asn-lle-Gly-Leu-Arg-Cys-Cys-Tyr- Gly-Ala-Arg-Cys-Tyr-Cys-Lys-Glu-Lys-Leu-Ser-Cys-Arg-Tyr-Asn-Arg-Val-Thr-Arg-Lys- Arg-Asp-Cys-Gly-Trp-Ser-Ser-Tyr-Asp-Cys-Lys-Cys-Asp-Tyr-Thr-Trp-Met-His-Arg-lle- Asp-Asp-Trp-Arg-lle-Asp-Asp-Trp-Arg-Leu-Asp-Gly-Tyr-Ser-Cys-Tyr-Cys-Lys-Glu-$CO_2H$ VII. Filistata peptide 14-1 has the following N-terminal amino acid sequence, SEQ ID NO:7.
$H_2N$-Glu-Glu-Lys-Lys-Cys-Lys-Leu-lle-Asp-Glu-Pro-Cys-Ser-Asn-Lys-Asp-Pro-lle-lle- Cys-Cys-Lys-Gly-Ala-Arg-Cys-Val-Cys-Asn-Asp-Val-Arg-Ser-Gly-Thr-Ser-Lys-Asp-Tyr- Leu-Gly-Arg-Asn-lle-Pro-Ala-Phe-Val-Arg-Val-Cys-Lys-Cys-Asp-Trp-Ser-Tyr-Pro-Ala-Tyr- Leu-Lys-Asp-Leu-Ala-Thr-Phe-Phe-Asn-Cys-Asn-Cys-Arg-$CO_2H$ The polypeptides of this invention block calcium channels in cells. Accordingly, these polypeptides are useful in blocking calcium channels in cells, per se. These polypeptides are also useful in the control of invertebrate pests and in the treatment of diseases and conditions in a mammal mediated by calcium channel function in cells.

Also within the scope of this invention are polypeptides which have substantially the same amino acid sequence and substantially the same calcium channel blocking activity as the polypeptide described above.

This invention also concerns pharmaceutical compositions comprising said polypeptides and methods of administering said polypeptides.

DETAILED DESCRIPTION OF THE INVENTION

Venom is obtained from the *Filistata hibernalis* spider through the process of milking by electrical stimulation according to standard methods well known to those skilled in the art. It is preferred that the method employed is one which safeguards against contamination of the whole venom by abdominal regurgitant or hemolymph. Such methods are well known to those skilled in the art. The whole venom so obtained is stored in a frozen state at about −78° C. until used for purification as described below. Purification of the constituents from the whole venom is accomplished by reverse phase high performance liquid chromatography (HPLC) on a variety of preparative and semi-preparative columns such as C-4 and C-18 Vydac® columns (Rainin Instrument Co. Inc., Mack Road, Woburn Mass. 01801). Peak detection is carried out monochromatically at 220–230 nm. Further analysis of the fractions can be accomplished with, for example, polychrome UV data collected with a Waters 990 diode array detector (Millipore Corporation, Waters Chromatography Division, 34 Maple Street, Milford, Mass. 01757). The fractions from the columns are collected by known methods such as through the use of an ISCO/

"FOXY" fraction collector and an ISCO 2159 peak detector (ISCO, 4700 Superior, Lincoln, Neb. 68504). The fractions are collected in appropriately sized vessels such as sterile polyethylene laboratoryware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

The polypeptides of the invention are sequenced according to known methods. A general strategy for determining the primary structure includes, for example, the following steps. 1) Reduction and S-pyridylation of disulfide-bridged cysteine residues to enhance substrate susceptability to enzymatic attack. 2) Controlled cleavage of the peptide through single or multi-step enzymatic digestion. 3) Isolation and purification of peptide fragments via reverse phase high performance liquid chromatography (HPLC). 4) Characterization of peptide fragments through N-terminal sequencing and ion-spray mass spectrometry.

S-pyridylethylation of cysteine residues of the polypeptides under study can be performed, for example, in solution followed by amino acid sequencing of the polypeptides. One such procedure for S-pyridylethylation can be accomplished as described below.

About 1 to 10 $\mu$g of polypeptide is dissolved or diluted in up to 50 $\mu$l of a buffer prepared by mixing 1 part 1M TrisHCl, pH 8.5, containing 4 mM EDTA and 3 parts 8M guanidine HCl. 2.5 $\mu$l of 10% aqueous 2-mercaptoethanol is added and the mixture is incubated at room temperature in the dark under argon for two hours. After incubation, 2 $\mu$l of 4-vinylpyridine (fresh reagent stored under argon at $-20°$ C.) is added and the mixture is incubated for another two hours at room temperature in the dark under argon. The mixture is then desalted, preferably by chromatography on a short, reverse phase column. The recovered alkylated polypeptide is then sequenced according to known methods.

In practicing this invention and employing the general procedure outlined above, it has been found that a suitable column for initial fractionation of the venom is a semi-preparative polysulfoethyl aspartamide column (PolyLC 9.4×200 mm, 5$\mu$). That column is eluted at a flow rate of 3.5 ml/minute using a triphasic linear gradient program beginning with 20% B, 80% C and 0% D and ending with 20% B, 0% C and 80% D over 45 minutes (B=$CH_3CN$, C=5 mM $H_3PO_4/H_2O$ at pH 4.5, D=C+1M NaCl), with detection at 220 nm. The desired fractions can then be further purified, for example, by application to a reversed phase HPLC column such as Vyda® C-18, 300 Å, 22×250 mm, with a flow rate of 15 ml/minute using a biphasic linear gradient program with 0.1% trifluoroacetic acid and $CH_3CN$, as set forth in the examples.

Given the benefit of the disclosure herein with respect to the peptides present in fractions 10, 12, 13-1, 13-2,13-3, 13-4 and 14-1, SEQ ID NO:1 to 7, respectively, of venom from *Filistata hibernalis*, it is now possible to obtain said peptides by methods other than through isolation/purification from whole venom. The polypeptides of this invention can be produced using recombinant DNA techniques through the cloning of a coding sequence for said polypeptides or portions thereof. For example, hybridization probes which take advantage of the now known amino acid sequence information of said polypeptides can be employed according to methods well known to those skilled in the art to clone a coding sequence for the entire polypeptide. A combination of recombinant DNA techniques and in vitro protein synthesis can also be employed to produce the polypeptides of this invention. Such in vitro protein synthesis methods include, but are not limited to, use of an ABI 430A solid phase peptide synthesizer (Applied Biosystems, Inc., 850 Lincoln Center Drive, Foster City, Calif. 94404) employing standard Merrifield chemistry or other solid phase chemistries well known to those skilled in the art.

It is well known in the art that certain amino acid substitutions can be made in polypeptides which do not affect, or do not substantially affect, the function of said polypeptides. The exact substitutions which are possible vary from polypeptide to polypeptide. Determination of permissible substitutions is accomplished according to procedures well known to those skilled in the art. Thus, all polypeptides having substantially the same amino acid sequence and substantially the same calcium channel blocking activity are within the scope of this invention.

The polypeptides of this invention irreversibly block calcium channels present in a variety of cells such as cells in the nervous and muscular system of invertebrates and vertebrates.

The ability of the polypeptides of this invention to block calcium channels is demonstrated by the following procedure. Cerebellar granule cells are prepared from the cerebellum of 8 day old rats (Wilkin et al., *Brain Res*, 115, 181–199, 1976). Squares (1 $cm^2$) of Aclar (Proplastics Inc., 5033 Industrial Ave., Wall, N.J. 07719) are coated with poly-L-lysine and placed in 12-well dishes that contain 1 ml of Eagles Basal Medium. The cells are dissociated and aliquots containing 6.25×106 cells are added to each well containing the squares of Aclar. Cytosine-beta-D-arabino furanoside (final concentration 10 $\mu$M) is added 24 hours after plating. The cells are used for fura2 analysis at 6, 7 and 8 days of culture. The cells (attached to the Aclar squares) are transferred to 12 well dishes containing 1 ml of 2 $\mu$M fura2/AM (Molecular Probes Inc., Eugene, Oreg. 97402) in HEPES buffer (containing 0.01% bovine serum albumin, 0.01% dextrose, pH 7.4, magnesium-free). The cells are incubated for 40 minutes at 37° C.; the fura2/AM-containing buffer is removed and replaced with 1 ml of the same buffer without fura2/AM. To a quartz cuvette is added 2.0 ml of prewarmed (37° C.) buffer. The cells on the Aclar are placed in the cuvette and the cuvette is inserted in a thermostatted (37° C.) holder equipped with a magnetic stirrer and the fluorescence is measured with a fluorescence spectrophotometer (Biomedical Instrument Group, University of Pennsylvania). The fluorescence signal is allowed to stabilize for about two minutes. Then 5–20 $\mu$l of a stock solution of the compound under study in phosphate buffered saline (PBS, pH 7.4) at appropriate concentration is added to the cuvette. Calibration of the fluorescent signals and fura2/AM leakage correction are performed using the established procedures of Nemeth et al., *J. Biol. Chem.*, 262, 5188 (1987) at the completion of each test. The maximum fluorescence value (Fmax) is determined by addition of ionomycin (35 $\mu$M) and the minimum fluorescence value (Fmin) is determined by the subsequent addition of EGTA (12 mM) to chelate calcium. Employing the foregoing procedure, calcium channel blocking by a subject polypeptide is shown to occur by a decrease in fluorescence upon addition of the subject polypeptide. The polypeptides of the invention exhibit low $IC_{50}$ values, including values under 0.3 nm, for blocking calcium channels using this assay. For comparison, two known commercial calcium channel antagonists, Nifedipine and Verapamil, have $IC_{50}$ values of 33 nm and 4800 nm, respectively.

The polypeptides of this invention are useful as calcium channel blockers in cells, per se. As such, these compounds are also useful in the control of invertebrate pests and in the treatment of diseases and conditions mediated by calcium channels function in cells in a mammal such as angina, hypertension, cardiomyopathies, supraventricular arrhythmias, aesophogeal achalasia, premature labor and Raynaud's disease. Further, these compounds are useful in the study of the physiology of cells including, but not limited to, cells of the nervous and muscular system.

Also within the scope of this invention are the pharmaceutically acceptable salts of the polypeptides of this invention. Such salts are formed by methods well known to those skilled in the art. For example, base salts of the polypeptides can be prepared according to conventional methods.

When a polypeptide of this invention is to be administered to a mammal, it can be administered alone or in combination with pharmaceutically acceptable carriers or diluents in a pharmaceutical composition according to standard pharmaceutical practice. The polypeptides can be administered orally or parenterally with the parenteral route of administration being preferred for polypeptides. Parenteral administration includes intravenous, intramuscular, intraperitoneal, subcutaneous and topical administration.

For oral use of a polypeptide of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polypeptide or salt thereof of this invention is used in a human subject, the daily dosage will normally be determined by the prescribing physician. Moreover, the dosage will vary according to the age, weight and response of the individual patient, as well as the severity of the patient's symptoms and the potency of the particular compound being administered.

When a polypeptide or salt thereof of this invention is used in control of invertebrate pests, said polypeptide is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polypeptide or salt thereof of this invention is used in the physiological study of cells, said polypeptide is administered to the cells according to methods well known to those skilled in the art. For example, said polypeptide can be administered to cells in an appropriate physiological buffer. An appropriate concentration of the compounds of this invention for use in such studies is 100 $\mu$M. However, the concentration of said polypeptide in such studies may be greater than or much less than 100 $\mu$M. The amount of the compound administered will be determined by the person skilled in the art according to well known methods.

The following Examples are illustrative and are not to be construed as limiting the scope of this invention.

Example 1, Peptide 10

A. Crude *Filistata hibernalis* (DW) venom (~80 $\mu$l) was applied to a semi-prep polysulfoethyl (PolyLC 9.4×200 mm, 5$\mu$) aspartamide column operated using a triphasic linear gradient program from 20% B, 80% C and 0% D to 20% B, 0% C and 80% D over 45 minutes (B=CH$_3$CN, C=5 mM H$_3$PO$_4$/H$_2$O at pH 4.5 and D=C+1M NaCl), with detection at 220 nm and a flow rate of 3.5 ml/minute. The desired fraction was collected from 38.5 to 40 minutes. Pooled fractions were desalted without concentration.

B. The material from the fractionation of step A, above, derived from 3360 $\mu$l of crude venom, was applied to a reversed phase HPLC column (Vydac®, C-18, 300 Å, 22×250 mm) operated using a biphasic linear gradient program from 80% A and 20% B to 56% A and 44% B over 42 minutes (A=0.1% trifluoroacetic acid and B=CH$_3$CN) with detection at 220 nm and a flow rate of 15 ml/minute. The desired fraction was collected from 13 to 14 minutes. Pooled like fractions from individual runs were concentrated by lyophilization.

The structure of peptide 10 was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/pyridylethylated peptide. Mass spectral analysis data was obtained from a SCI-EX API III ion spray mass spectrometer.

The data taken together affirm the structure of peptide 10 as shown below.
SEQ ID NO:1, 72 residues, 12 cysteines, 6 disulfide bonds.
Calculated mass=8699.18.
Observed mass=8698.36 (ion-spray mass spec.).
Estimated pI=8.05.

Example 2, Peptide 12

A. Crude *Filistata hibernalis* (DW) venom (~80 $\mu$l) was applied to a semi-prep polysulfoethyl (PolyLC 9.4×200 mm, 5$\mu$) aspartamide column operated using a triphasic linear gradient program from 20% B, 80% C and 0% D to 20% B, 0% C and 80% D over 45 minutes (B=CH$_3$CN, C=5 mM H$_3$PO$_4$/H$_2$O at pH 4.5 and D=C+1M NaCl), with detection at 220 nm and a flow rate of 3.5 ml/minute. The desired fraction was collected from 32 to 33 minutes. Pooled fractions were desalted without concentration.

B. The material from the fractionation of step A, above, derived from 3360 $\mu$l of crude venom, was applied to a reversed phase HPLC column (Vydace, C-18, 300 Å, 22×250 mm) operated using a biphasic linear gradient program from 80% A and 20% B to 56% A and 44% B over 42 minutes (A=0.1% trifluoroacetic acid and B=CH$_3$CN) with detection at 220 nm and a flow rate of 15 ml/minute. The desired fraction was collected from 16 to 17 minutes. Pooled like fractions from individual runs were concentrated by lyophilization.

The structure of peptide 12 was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/pyridylethylated peptide. Mass spectral analysis data was obtained from a SCI-EX API III ion spray mass spectrometer.

A pyridylethylated derivative of peptide 12 suitable for N-terminal sequencing was prepared in the following fashion. Peptide 12 (100 μg) was dissolved in 10 μl of buffer (1:3 ratio of 1M tris, pH 8.4, 4 μM EDTA-dibasic and 8M guanidine-hydrochloride and was treated with 2.4 μl of a 1.41M (10% v/v) solution of 2-mercaptoethanol in buffer and kept for 3 hours in the dark at room temperature. The reaction mixture was then treated with 3.7 μl of a 0.93M solution of 4-vinylpyridine in buffer and kept at room temperature in the dark for 18 hours. The reaction mixture was diluted with 184 μl of 10% $CH_3CN/H_2O$ and applied to an HPLC column (Baker WPC-18, 4.6×250 mm) operated using a biphasic linear gradient program of 100 to 65% A and 0 to 35% B over 30 minutes followed by 65 to 40% A and 35 to 60% B over 15 minutes (A=0.1% trifluoroacetic acid, B=$CH_3CN$) with detection at 220 nM and a flow rate of 1.0 ml/minute. The desired fraction was collected at 32.5 to 33.5 minutes and was concentrated by lyophilization. Approximate yield (based on amino acid analysis), 82.36 μg.

The data taken together affirm the structure of peptide 12 as shown below.
SEQ ID NO:2, 74 residues, 12 cysteines, 6 disulfide bonds.
Calculated mass=8739.38 (acid).
Observed mass=8738.47±0.98 (ion-spray mass spec.).
Estimated pI=8.20.

Example 3, Peptide 13-1

A. Crude *Filistata hibernalis* (DW) venom (~80 μl) was applied to a semi-prep polysulfoethyl (PolyLC 9.4×200 mm, 5μ) aspartamide column operated using a triphasic linear gradient program from 20% B, 80% C and 0% D to 20% B, 0% C and 80% D over 45 minutes (B=$CH_3CN$, C=5 mM $H_3PO_4/H_2O$ at pH 4.5 and D=C+1M NaCl), with detection at 220 nm and a flow rate of 3.5 ml/minute. The desired fraction was collected from 34 to 35.5 minutes. Pooled fractions were desalted without concentration.

B. The material from the fractionation of step A, above, derived from 3360 μl of crude venom, was applied to a reversed phase HPLC column (Vydace®, C-18, 300 Å, 22×250 mm) operated using a biphasic linear gradient program from 75% A and 25% B to 70% A and 30% B over 60 minutes (A=0.1% trifluoroacetic acid and B=$CH_3CN$) with detection at 220 nm and a flow rate of 15 ml/minute. The desired fraction was collected from 25.5 to 28.5 minutes. Pooled like fractions from individual runs were concentrated by lyophilization to yield a mixture of peptides 13-1 and 13-2.

The structure of peptide 13-1 was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/pyridylethylated peptide. Mass spectral analysis data was obtained from a SCI-EX API III ion spray mass spectrometer.

A pyridylethylated derivative of peptide 13-1 suitable for N-terminal sequencing was prepared in the following fashion. Peptide 13-1 (150 μg) was dissolved in 10 μl of buffer (1:3 ratio of 1M tris, pH 8.4, 4 μM EDTA-dibasic and 8M guanidine hydrochloride and was treated with 3.65 μl of a 1.41M (10% v/v) solution of 2-mercaptoethanol in buffer and kept for 3 hours in the dark at room temperature. The reaction mixture was then treated with 5.91 μl of a 0.93M solution of 4-vinylpyridine in buffer and kept at room temperature in the dark for 18 hours. The reaction mixture was diluted with 280 μl of 10% $CH_3CN/H_2O$ and applied to an HPLC column (Baker WPC-18, 4.6×250 mm) operated using a biphasic linear gradient program of 100 to 65% A and 0 to 35% B over 30 minutes followed by 65 to 40% A and 35 to 60% B over 15 minutes (A=0.1% trifluoroacetic acid, B=$CH_3CN$) with detection at 220 nM and a flow rate of 1.0 ml/minute. The desired fraction was collected at 33 to 34.5 minutes and was concentrated by lyophilization. Approximate yield (based on amino acid analysis), 79.4 μg.

Due to the homology of peptides 13-1 and 13-2, these peptides were not separated by ion exchange or reverse phase chromatography. Initial sequencing of the mixture found the first 50 amino acids to be identical, suggesting the use of peptide degradation to complete structure elucidation. Digestion of the mixture with Glu-C, followed by sequencing of the resultant fractions, coupled with further digestion with trypsin in 0.1M tris-HCl, 1M guanidine HCl at pH 8.5, followed by mass spectrometric analysis and sequencing confirmed the structure of peptide 13-1 as shown below.
SEQ ID NO:3, 74 residues, 12 cysteines, 6 disulfide bonds.
Calculated mass=8653.26.
Observed mass 8652.57±0.87 (ion-spray mass spec.).
Estimated pI=7.65.

Example 4, Peptide 13-2

The structure for fraction 13-2 was confirmed as described above in Example 3
SEQ ID NO:4, 74 residues, 12 cysteines, 6 disulfide bonds.
Calculated mass 8680.29.
Observed mass 8678.64±1.64 (ion-spray mass spec.).
Estimated pI=7.65.

Example 5, Peptide 13-3

A. Crude *Filistata hibernalis* (DW) venom (~80 μl) was applied to a semi-prep polysulfoethyl (PolyLC 9.4×200 mm, 5μ) aspartamide column operated using a triphasic linear gradient program from 20% B, 80% C and 0% D to 20% B, 0% C and 80% D over 45 minutes (B=$CH_3CN$, C=5 mM $H_3PO_4/H_2O$ at pH 4.5 and D=C+1M NaCl), with detection at 220 nm and a flow rate of 3.5 ml/minute. The desired fraction was collected from 34 to 35.5 minutes. Pooled fractions were desalted without concentration.

B. The material from the fractionation of step A, above, derived from 3360 μl of crude venom, was applied to a reversed phase HPLC column (Vydac®, C-18, 300 Å, 22×250 mm) operated using a biphasic linear gradient program from 75% A and 25% B to 70% A and 30% B over 60 minutes (A=0.1% trifluoroacetic acid and B=$CH_3CN$) with detection at 220 nm and a flow rate of 15 ml/minute. The desired fraction was collected from 29 to 31 minutes. Pooled like fractions from individual runs were concentrated by lyophilization.

The structure of peptide 13-3 was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/pyridylethylated peptide. Mass spectral analysis data was obtained from a SCI-EX API III ion spray mass spectrometer.

A pyridylethylated derivative of peptide 13-3 suitable for N-terminal sequencing was prepared in the following fashion. Peptide 13-3 (300 µg) was dissolved in 20 µl of buffer (1:3 ratio of 1M tris, pH 8.4, 4 µM EDTA-dibasic and 8M guanidine-hydrochloride and is treated with 7.28 µl of a 1.41M (10% v/v) solution of 2-mercaptoethanol in buffer and kept for 3 hours in the dark at room temperature. The reaction mixture was then treated with 11.19 µl of a 10% v/v solution of 4-vinylpyridine in buffer and kept at room temperature in the dark for 18 hours. The reaction mixture was diluted to 600 µl with 1% TFA/H$_2$O and applied to an HPLC column (Baker WPC-18, 4.6×250 mm) operated using a biphasic linear gradient program of 100 to 65% A and 0 to 35% B over 30 minutes followed by 65 to 40% A and 35 to 60% B over 15 minutes (A=0.1% trifluoroacetic acid, B=CH$_3$CN) with detection at 220 nM and a flow rate of 1.0 ml/minute. The desired fraction was collected at 34 to 35 minutes and was concentrated by lyophilization. Approximate yield (based on amino acid analysis), 194 µg.

The data taken together affirm the structure of peptide 13-3 as shown below.
SEQ ID NO:5, 74 residues, 12 cysteines, 6 disulfide bonds.
Calculated mass 8668.29.
Observed mass 8668 (ion-spray mass spec.).
Estimated pl=7.65.

Example 6, Peptide 13-4

A. Crude *Filistata hibernalis* (DW) venom (~80 µl) was applied to a semi-prep polysulfoethyl (PolyLC 9.4×200 mm, 5µ) aspartamide column operated using a triphasic linear gradient program from 20% B, 80% C and 0% D to 20% B, 0% C and 80% D over 45 minutes (B=CH$_3$CN, C=5 mM H$_3$PO$_4$/H$_2$O at pH 4.5 and D=C+1M NaCl), with detection at 220 nm and a flow rate of 3.5 ml/minute. The desired fraction was collected from 34 to 35.5 minutes. Pooled fractions were desalted without concentration.

B. The material from the fractionation of step A, above, derived from 3360 µl of crude venom, was applied to a reversed phase HPLC column (Vydac®, C-18, 300 Å, 22×250 mm) operated using a biphasic linear gradient program from 75% A and 25% B to 70% A and 30% B over 60 minutes (A=0.1% trifluoroacetic acid and B=CH$_3$CN) with detection at 220 nm and a flow rate of 15 ml/minute. The desired fraction was collected from 22 to 22.5 minutes. Pooled like fractions from individual runs were concentrated by lyophilization.

The structure of peptide 13-4 was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/pyridylethylated peptide. Mass spectral analysis data was obtained from a SCI-EX API III ion spray mass spectrometer. The data taken together affirm the structure of peptide 13-4 as shown below.
SEQ ID NO:6, 72 residues, 12 cysteines, 6 disulfide bonds.
Calculated mass 8640.15.
Observed mass 8640 (ion-spray mass spec.).
Estimated pl=7.87.

Example 7, Peptide 14-1

A. Crude *Filistata hibernalis* (DW) venom (~80 ml) was applied to a semi-prep polysulfoethyl (PolyLC 9.4×200 mm, 5µ) aspartamide column operated using a triphasic linear gradient program from 20% B, 80% C and 0% D to 20% B, 0% C and 80% D over 45 minutes (B=CH$_3$CN, C=5 mM H$_3$PO$_4$/H$_2$O at pH 4.5 and D=C+1M NaCl), with detection at 220 nm and a flow rate of 3.5 ml/minute. The desired fraction was collected from 28 to 29 minutes. Pooled fractions were desalted without concentration.

B. The material from the fractionation of step A, above, derived from 3360 µl of crude venom, was applied to a reversed phase HPLC column (Vydac®, C-18, 300 Å, 22×250 mm) operated using a biphasic linear gradient program from 80% A and 20% B to 56% A and 44% B over 42 minutes (A=0.1% trifluoroacetic acid and B=CH$_3$CN) with detection at 220 nm and a flow rate of 15 ml/minute. The desired fraction was collected from 18 to 19.5 minutes. Pooled like fractions from individual runs were concentrated by lyophilization.

The structure of peptide 14-1 was determined and verified by the following methods. PTC amino acid analysis was carried out on 1 to 10 nmols in triplicate using the Waters Pico-Tag system. N-terminal sequencing was carried out on a pulse-liquid sequenator (ABI) both on native and on reduced/pyridylethylated peptide. Mass spectral analysis data was obtained from a SCI-EX API III ion spray mass spectrometer.

A pyridylethylated derivative of peptide 14-1 suitable for N-terminal sequencing was prepared in the following fashion. Peptide 14-1 (150 µg) was dissolved in 10 µl of buffer (1:3 ratio of 1M tris, pH 8.4, 4 µM EDTA-dibasic and 8M guanidine hydrochloride and was treated with 3.65 µl of a 1.41M (10% v/v) solution of 2-mercaptoethanol in buffer and kept for 3 hours in the dark at room temperature. The reaction mixture was then treated with 5.91 of a 0.93M solution of 4-vinylpyridine in buffer and kept at room temperature in the dark for 18 hours. The reaction mixture was diluted with 280 µl of 10% CH$_3$CN/H$_2$O and applied to an HPLC column (Baker WPC-18, 4.6×250 mm) operated using a biphasic linear gradient program of 100 to 65% A and 0 to 35% B over 30 minutes followed by 65 to 40% A and 35 to 60% B over 15 minutes (A=0.1% trifluoroacetic acid, B=CH$_3$CN) with detection at 220 nM and a flow rate of 1.0 ml/minute. The desired fraction was collected at 33 to 34.5 minutes and was concentrated by lyophilization.

The sequence of this peptide had been determined unambiguously up to residue 52. In 25 mM tris HCl, 1 mM EDTA at pH 8.5, 20 µg of reduced and pyridylethylated peptide was digested with 2 µg of the endoproteinase Lys-C. Characterization by sequencing and ion-spray mass spectrometry provided the complete primary structure peptide 14-1 as shown below.

SEQ ID NO:7, 73 residues, 10 cysteines, 5 double bonds.

Calculated mass 8308.05.

Observed mass 8307.67±0.55 (ion-spray mass spec.).

Estimated pl=8.17.

We claim:

1. A purified polypeptide having the amino acid sequence, SEQ ID NO:1, SEQ ID NO:2, SEQ ID NO:3, SEQ ID NO:4, SEQ ID NO:5, SEQ ID NO:6 or SEQ ID NO:7, or a pharmaceutically acceptable salt thereof.

2. A method of blocking calcium channels in a cell comprising administering to said cell a calcium channel blocking amount of a polypeptide according to claim 1.

* * * * *